United States Patent [19]
Carroll

[11] Patent Number: 5,605,691
[45] Date of Patent: Feb. 25, 1997

[54] IMMUNOLOGICALLY ACTIVE PROTEINS FROM INCLUSION BODIES

[75] Inventor: Sean B. Carroll, Cottage Grove, Wis.

[73] Assignee: Ophidian Pharmaceuticals, Inc., Madison, Wis.

[21] Appl. No.: 129,027

[22] Filed: Sep. 29, 1993

Related U.S. Application Data

[63] Continuation of Ser. No. 946,927, Sep. 17, 1992, abandoned.

[51] Int. Cl.$^6$ ............................. A61K 39/00; C07K 1/14; C07K 1/22
[52] U.S. Cl. ...................... 424/184.1; 530/412; 530/413; 435/69.1; 435/69.3
[58] Field of Search ...................... 435/814, 815, 435/816, 69.1, 69.3; 424/88, 92, 858, 86, 184.1; 530/384.1, 412, 413; 436/501, 532, 518, 524, 533, 527, 534, 528; 535/60, 61

[56] References Cited

U.S. PATENT DOCUMENTS

| | | | |
|---|---|---|---|
| 4,511,502 | 4/1985 | Builder et al. | 530/417 |
| 4,511,503 | 4/1985 | Olson et al. | 530/422 |
| 4,512,922 | 4/1985 | Jones et al. | 530/408 |
| 4,518,526 | 5/1985 | Olson | 530/351 |
| 4,604,377 | 8/1986 | Fernandes et al. | 514/2 |
| 4,677,196 | 6/1987 | Rausch et al. | 435/69.4 |
| 4,678,553 | 7/1987 | Mandle et al. | 204/522 |
| 4,735,800 | 4/1988 | Collett et al. | 424/186.1 |
| 4,766,224 | 8/1988 | Rausch | 530/412 |
| 4,801,691 | 1/1989 | Auer | 530/399 |
| 4,931,543 | 6/1990 | Halenbeck et al. | 530/351 |
| 5,019,508 | 5/1991 | Johnson et al. | 435/198 |
| 5,101,018 | 3/1992 | Mehrotra et al. | 530/399 |
| 5,109,121 | 4/1992 | Blum et al. | 530/420 |
| 5,196,193 | 3/1993 | Carroll | 424/172.1 |

OTHER PUBLICATIONS

Ausubel, F. M. et al. 1988. Current Protocols in Molecular Biology vol. 2.
John Wiley & Sons, New York, pp. 10.2.1–10.2.9 and 10.5.1–10.5.5.
Edens, R. E. et al. 1990. J. Immunol. Meth. vol. 133 pp. 67–70.
Neugebauer, J. M. 1990, "Detergents: an overview", Methods Enzymol vol. 182 pp. 239–253.
Knuth, M. W. et al. 1987. "Purification of Proteins in the Denatured State". *Protein Purification: Micro to Macro,* ed. R. Burgess, Alan R. Liss, NY, pp. 297–305.
Weber, K., and M. Osborn. In: The Proteins, ed. H. Neurath, Academic Press, New York. vol. 1, pp. 179–223.
Jaenicke, R, and R. Rudolph. In: Protein Structure, a Practical Approach, ed. T. E. Creighton, IRL Press, Oxsford, pp. 191–223.
F. A. O. Marston, Biochem. J. 240:1 (1986).
C. H. Schein, Biotechnology 7:1141 (1989).
Bruggemann et al., BioTechniques 10:202 (1991).
D. L. Wilkinson and R. G. Harrison, Biotechnology 9:443 (1991).
F. A. O. Marston, In: *DNA Cloning: A Practical Approach,* vol. III (D. Glover, ed.) (IRC Press) (1989) pp. 59.
J. Krueger et al., BioPharm. 2:40 (1989).
Soutschek et al., J. of Chrom. 521:267 (1990).
A. C. Issekutz, J. of Immunological Methods 61:275 (1983).
Rosenberg et al., Gene 56:125 (1987).
A. S. Laughon, and M. P. Scott, Nature 310:25 (1984).
F. W. Studier et al., Methods of Enzymology 185:60 (1990).
B. S. Thalley and S. B. Carroll, BioTechnology 8:934 (1990).
H. Towbin et al., Proc. Natl. Acad. Sci. USA 76:4350 (1979).
S. Carroll and M. P. Scott, Cell 43:47 (1985).
D. Tautz, Nature 332:281 (1988).
J. Pankratz et al., Cell 61:309 (1990).
U. Gaul et al., Cell 50:639 (1987).
R. Kraut and M. Levine, Development 111:601 (1991).
O. Kapp and S. Vinogradov, Anal. Biochem. 91:230 (1978).
G. Tuszynski and L. Warren, Anal. Biochem. 67:55 (1975).
S. B. Carroll and A. S. Laughon, In: *DNA Cloning: A Practical Approach,* vol. III, Production and Purification of Polyclonal Antibodies to the Foreign Segment of β–galactosidase Fusion Proteins (D. Glover, ed.) (IRL Press Oxford) (1987), pp. 89–111.
K. Talmadge and C. Siebert, J. Chromatography 476:175 (1989).
D. Rifkind and J. Palmer, J. Bacter. 92:815 (1966).

*Primary Examiner*—Mary E. Mosher
*Attorney, Agent, or Firm*—Medlen & Carroll, LLP

[57] ABSTRACT

This invention relates to the conversion of denatured proteins to soluble forms which are suitable for injection of humans and other animals. The invention is also suitable for analytical use. This method is applicable to the efficient solubilization of proteins which have varying degrees of solubility.

13 Claims, 6 Drawing Sheets

IMMUNOLOGICALLY ACTIVE PROTEINS FROM INCLUSION BODIES

This is a Continuation of application Ser. No. 07/946,927 filed on Sep. 17, 1992, now abandoned.

FIELD OF THE INVENTION

The present invention relates to converting denatured protein to a soluble form suitable for injection into humans and animals as well as for analytical use.

BACKGROUND OF THE INVENTION

Eukaryotic proteins having clinical or industrial value may be obtained in large quantities using techniques which facilitate their synthesis in bacteria or in eukaryotic cell cultures. However, once synthesized, there are often problems recovering these recombinant proteins in substantial yields and in a useful form. Recombinant proteins expressed in bacteria often accumulate in the bacterial cytoplasm as insoluble aggregates known as inclusion bodies (F. A. O. Marston, Biochem. J. 240:1–12 (1986); C. H. Schein, Biotechnology 7:1141–1149 (1989)). In order to effectively utilize the protein for immunochemical manipulations, the protein must be recovered in a soluble form which is immunologically active.

Proteins have been solubilized using guanidinium salts, urea, detergents, or other organic solvents. However, the efficacy of the solubilizing agent appears to vary along with the physical characteristics of the protein. It also has been suggested that 0.01–2% Triton or SDS detergents can also be used to denature inclusion body proteins, (Bruggeman et al., Biotechniques 10:202–209 (1991)), however, this concentration range is insufficient for very insoluble inclusion body proteins. There is no general method of solubilization that works for most proteins. (D. L. Wilkinson and R. G. Harrison, Biotechnology 9:443–448 (1991); F. A. O. Marston, in: *DNA Cloning: A Practical Approach*, Vol. III, (D. Glover, ed.), IRC Press pp. 59–88 (1989)).

Some techniques for solubilizing inclusion body proteins initially require a strong denaturing solution to solubilize the protein and subsequently require at least a non-ionic, weaker denaturing solution to maintain the protein solubility. (Builder & Ogez, U.S. Pat. No. 4,511,502 (1985); Olson, U.S. Pat. No. 4,518,526 (1985); Olson & Pai, U.S. Pat. No. 4,511,503 (1985); Jones et al., U.S. Pat. No. 4,512,922 (1985)).

The use of guanidinium salts and urea for solubilizing proteins has two problems. The first is that unless the protein concentration is dilute, the protein precipitates out of solution when the solubilizing agent is removed (J. Krueger et al., BioPharm. 2:40–45 (1989)). Solutions having protein concentrations of more than one milligram per milliliter are generally not handled successfully by this method (F. A. O. Marston, in: *DNA Cloning: A Practical Approach*, Vol. III, (D. Glover, ed.), IRC Press pp. 59–88 (1989)). The second problem is that use of guanidinium salts and urea precludes subsequent chemistry involving binding of a protein's reactive amine groups, since the urea and guanidinium salts have reactive primary amines that swamp those of the protein. One chemical method that requires reactive amine groups is the preparation of affinity matrices that bind a protein to an inert support by a chemical bond between a primary amine group on the protein and an activated group on the support.

Recombinant transmembrane proteins which contain both hydrophobic and hydrophilic regions are especially intractable to solubilization. The protein gp41 is a component of the viral envelope of the human immunodeficiency virus (HIV) and is useful for the sensitive and specific detection of anti-HIV antibodies. Recombinant gp41 from *E. coli* inclusion bodies is extremely insoluble. The recombinant protein is insoluble at pH 8.9 in 8M urea or 7M guanidine-HCl, as well as in the non-ionic detergents 1.5% octyl B-D-glucopyranoside or 2% Triton X-100. To substantially solubilize the protein requires 8M urea or 6M guanidinium hydrochloride at pH 12.5. (Soutschek et al., J. of Chrom. 521:267 (1990)). This method would not meet the standard of safety required for injection of materials into humans because urea or guanidinium salts are required to maintain protein solubility but are not suitable for human injection. Therefore, this procedure would not be appropriate for recovering recombinant protein antigens for human vaccines against this AIDS virus component.

Additionally, biological products intended for injection must be free of bacterial endotoxins, the lipopolysaccharide component of the cell walls of gram negative bacteria. Endotoxin can produce pyrogenic and shock reactions after systemic administration. Therefore, where inclusion body protein is intended for systemic administration in humans or animals, the protein preparation must be in a form that can be treated to remove endotoxins.

What is needed is a protein solubilization method which maintains the protein in solution after removal of the solubilizing agent and preserves the immunological activity of the protein. Additionally, a method is needed whereby protein solubility is stabilized without the need for amine-containing denaturants which interfere with protein reactivity. Still further, a method is needed which is efficient for proteins having widely varying solubilities and adequate for very insoluble proteins.

SUMMARY OF THE INVENTION

The present invention relates to converting denatured protein to a soluble form suitable for injection into humans and animals as well as for analytical use.

The present invention contemplates a method for solubilizing inclusion body protein. In one embodiment, the method for solubilizing comprises: a) providing inclusion body protein; b) providing a solution of greater than 2% anionic detergent; and c) treating the inclusion body protein with the solution so that the inclusion body protein is solubilized. In one embodiment, step (a) comprises providing inclusion body protein treated with inclusion body purification means. It is desirable that the inclusion body purification means comprises washing inclusion bodies with a solution of approximately 0.1% SDS/1% Triton X-100/1% sodium deoxycholate. In another embodiment, the anionic detergent is selected from the group consisting of sodium dodecyl sulfate, sodium tetradecyl sulfate, and sodium hexadecyl sulfate. Preferably, the anionic detergent is approximately 10% sodium dodecyl sulfate. In another embodiment, the inclusion body protein is greater than 95% solubilized. In still another embodiment, the treating of step (c) further comprises heating the solution to approximately 95° C. for at least 5 minutes. In still another embodiment, the method for solubilizing further comprises: d) removing substantially all of the anionic detergent solution under conditions such that the solubilized protein remains solubilized. It is desirable that the method of solubilizing still further comprises: e) treating the inclusion body protein solution with pyrogen-removing means to provide a pharmaceutically acceptable solution which is pyrogen free.

The present invention also contemplates a method for solubilizing and maintaining the solubility of inclusion body protein. In one embodiment, the method for solubilizing and maintaining the solubility comprises: a) providing in any order: i) inclusion body protein, ii) first solution containing greater than 2% anionic detergent, and iii) a second solution which is free of reactive amine groups and contains less anionic detergent than the first solution; b) treating the inclusion body protein with the first solution so that the inclusion body protein is solubilized; and c) removing the detergent by dialysis of the first solution against the second solution under conditions such that the solubilized protein remains solubilized. In one embodiment, the second solution is free of anionic detergent. In another embodiment, the dialyzing comprises electrodialyzing. In still another embodiment, the second solution comprises successive solutions of decreasing percentage of anionic detergent and step (c) comprises successively dialyzing the solubilized inclusion body protein against the successive solutions.

The present invention also contemplates a method for solubilizing and maintaining the solubility of inclusion body protein, comprising: a) providing in any order: i) inclusion body protein, ii) a detergent solution containing greater than 2% anionic detergent, and iii) detergent removing means; b) treating the inclusion body protein with the detergent solution so that the inclusion body protein is solubilized; applying the inclusion body protein in the detergent solution to the detergent removing means; and d) removing substantially all of the detergent solution under conditions such that the solubilized protein remains solubilized. In one embodiment, the detergent removing means comprises a gel support with detergent-binding capability and step (d) comprises passing the inclusion body protein through the gel support under conditions that retain substantially all of the detergent on the gel support. In another embodiment, the method further comprises eluting substantially all of the anionic detergent from the gel support so that the detergent removing means is recyclable. Preferably, the gel support comprises an ion retardation resin.

The present invention also contemplates a method for immobilizing solubilized inclusion body protein. In one embodiment, the method for immobilizing comprises: a) providing: i) inclusion body protein, ii) a first solution containing greater than 2% anionic detergent, and iii) a second solution which is substantially free of reactive amine groups and contains less anionic detergent than the first solution; b) treating the inclusion body protein with the first solution so that the inclusion body protein is solubilized; c) replacing the first solution with the second solution under conditions such that the inclusion body protein remains solubilized; and d) attaching the solubilized inclusion body protein to the insoluble support. Preferably the attaching is covalent attaching. It is desirable that the insoluble support comprises a resin comprising aidehyde-activated agarose. Preferably, the anionic detergent is selected from the group consisting of sodium dodecyl sulfate, sodium tetradecyl sulfate, and sodium hexadecyl sulfate. More preferably, the anionic detergent is approximately 10% sodium dodecyl sulfate. It is desirable that greater than 50% of the inclusion body protein is attached to the insoluble support.

The present invention also contemplates a method of eliciting antibodies to solubilized inclusion body protein. In one embodiment the method of eliciting antibodies comprises: a) providing: i) inclusion body protein, ii) a first solution containing greater than 2% anionic detergent, iii) a second solution which is free of reactive amine groups and contains less anionic detergent than the first solution, and iv) a vertebrate species; b) treating the inclusion body protein with the first solution so that the inclusion body protein is solubilized; c) replacing the first solution with the second solution under conditions such that the inclusion body protein remains solubilized; and d) immunizing the vertebrate species with the inclusion body protein which is solubilized, so that reactive antibodies are produced. In one embodiment, the method further comprises the step: e) purifying the reactive antibodies. Preferably, step (e) comprises purifying the reactive antibodies by means of an antigen matrix comprising the solubilized inclusion body protein covalently attached to an insoluble support. It is desirable that the insoluble support comprises a resin comprising aidehyde-activated agarose.

DESCRIPTION OF THE DRAWINGS

FIG. 4 shows SDS-PAGE analysis of kni (FIG. 4A) and kr (FIG. 4B) protein from inclusion bodies solubilized with different concentrations of SDS solution.

FIG. 5 is a Western blot, showing the reactivity of anti-Kr antibody.

DESCRIPTION OF THE INVENTION

The present invention is directed to solubilized inclusion body proteins and methods of using solubilized inclusion body proteins to elicit and purify antibodies. The properties of solubilized inclusion body proteins prepared according to the present invention make them multipurpose; solubilized inclusion body proteins are useful for analytical studies in vitro and useful for immunizations.

The term "solubilize" as used herein in referring to inclusion body protein is defined as dissolving the protein in a fluid. "Maintaining the solubility of a protein" refers to maintaining a protein in a dissolved state.

The present invention contemplates solubilizing inclusion body protein in greater than 2% anionic detergent solution. The present invention also contemplates solubilizing inclusion body protein with heating, so that it is useful for general protein solubilizations. Purification of inclusion body protein prior to solubilization is also contemplated.

The present invention further contemplates removing substantially all of the detergent by a variety of means, while maintaining the protein solubilized in solution. In one embodiment, detergent removal is by dialysis. In another embodiment, detergent removal is by passage of the solubilized protein solution through a gel support with detergent-binding capacity.

The present invention further contemplates manipulating the solubilized protein. In one embodiment, the solubilized protein is used to immunize vertebrates to elicit antibodies. In another embodiment, the solubilized protein is attached to an insoluble support which may be used to purify antibodies. In still another embodiment, the solubilized protein is used for therapeutic infusion or injection, including vaccination.

The present invention also contemplates removal of pyrogen from inclusion body proteins solubilized in detergent solution. Pyrogen removal is by means of commercially available columns which bind endotoxin.

DETAILED DESCRIPTION OF THE INVENTION

Figure 1:
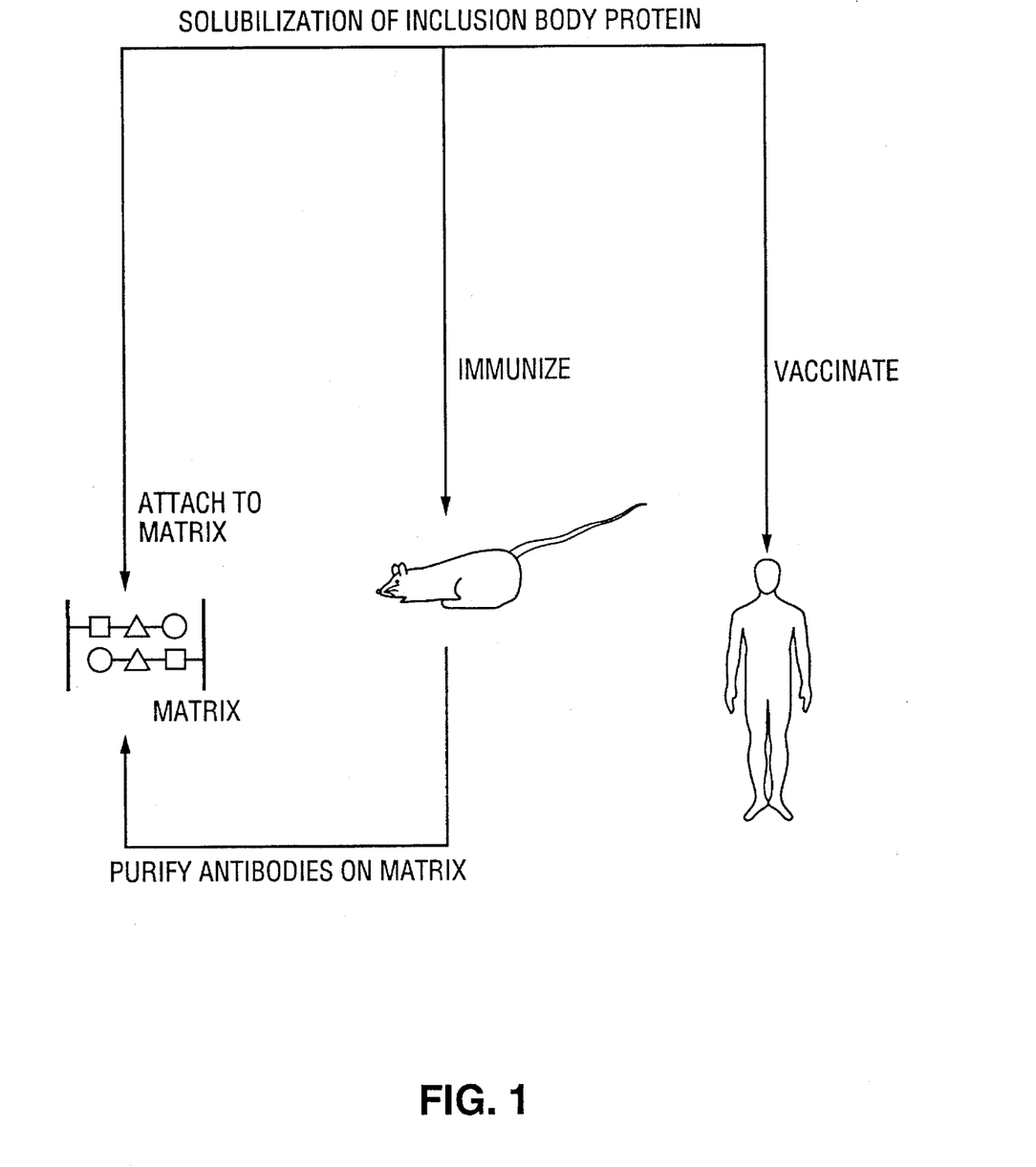
FIG. 1 is a schematic, showing a preferred embodiment of the method of the present invention.

The present invention contemplates (I) solubilizing and maintaining the solubility of a broad spectrum of inclusion body proteins and (II) injecting solubilized inclusion body proteins into vertebrates to elicit antibodies. The present invention further contemplates (III) purifying antibodies by binding to a matrix of antigenic inclusion body proteins. A preferred embodiment of the method of the present invention is shown in FIG. 1 illustrating the temporal relationship of the method steps. The individual steps are described separately below.

I. Solubilizing and Maintaining the Solubility of Inclusion Body Protein

The present invention contemplates a method for solubilizing inclusion body protein in a solution of greater than 2% anionic detergent. It is not intended that the present invention be limited to any particular anionic detergent. A preferred detergent is sodium dodecyl sulfate. Other anionic detergents are the sodium salts of caprylic acid, cholic acid, 1-decanesulfonic acid, deoxycholic acid, glycocholic acid, glycodeoxycholic acid, taurocholic acid, and taurodeoxycholic acid. The method of the invention contemplates all members of the family of sodium salts of sulfate detergents (e.g., sodium tetradecyl sulfate and sodium hexadecyl sulfate).

The method of the invention contemplates a detergent concentration greater than 2% in order to be applicable to a broad spectrum of proteins with differing solubilities, including those proteins that are generally difficult to solubilize. While 2% SDS is not sufficiently powerful to solubilize very insoluble inclusion body proteins (e.g., Drosophila kni protein), 10% SDS is effective. A preferred embodiment of the invention contemplates using approximately 10% SDS to solubilize inclusion body proteins. At this concentration, the method is generally applicable to a broad spectrum of proteins and, surprisingly, when SDS is removed from the solubilized protein solution, all the protein remains in solution.

When the inclusion body proteins do not solubilize readily in greater than 2% anionic detergent, the invention contemplates heating the inclusion body proteins in the greater than 2% anionic detergent solution until the proteins dissolve. This can be accomplished by heating to approximately 95° C. for at least 5 min.

In one embodiment, the method of the present invention contemplates providing purified inclusion body protein for solubilization. Purification is accomplished by washing the inclusion bodies with a solution of approximately 0.1% SDS/1% Triton X-100/1% sodium deoxycholate.

In another embodiment, the method of the present invention contemplates removing the detergent from the protein solution under conditions such that the inclusion body protein remains solubilized. The present invention contemplates that removal of the detergent may take place in one step or in several steps.

A preferred embodiment contemplates removal of the detergent by dialysis. As used herein, "dialysis" refers to a technique whereby the protein solution is separated from a dialysis solution by a barrier that is impermeable to the protein but permeable to detergent so that detergent diffuses across the barrier from an area of high concentration to an area of low concentration. Preferably, the dialysis solution is chosen to be compatible with affinity coupling chemistry and biocompatible for immunizations. Generally, a buffered solution at an appropriate ionic strength and pH is chosen. The dialysis solution may be supplemented with additives such as reductants, protease inhibitors, and chelators but not with compounds that contain reactive amine groups such as urea or guanidinium salts.

The invention contemplates that the protein solution will be dialyzed against a dialysis solution free of reactive amine groups and having a detergent concentration which is less than that of the protein solution and which may be zero. In one embodiment the invention contemplates a single step dialysis where the dialysis solution contains no detergent. An alternative embodiment contemplates successive equilibrium dialysis steps where the detergent concentration of the dialysis solution is lower than that of the protein solution and may be zero. Electrodialysis is also contemplated by the method of the invention.

It is not intended that the present invention be limited to dialysis apparatus to remove detergent from the solubilized inclusion body protein solution. In one embodiment, the method of the present invention contemplates removing detergent from the protein solution by means of an insoluble support comprising a gel with detergent-binding capability. In this embodiment, the protein solution (preferably diluted 1:10 with a non-detergent-containing diluent) is applied to a gel so that anionic detergent (now at a ten-fold lower concentration) is substantially retained by the gel while the protein passes through the gel. In another embodiment, after the protein passes through the gel, the detergent is eluted from the gel so that the gel is recyclable. Gels that have detergent-binding capability include Extracti-gel (Pierce, Rockford, Ill.), and ion retardation resins such as AG11A8 (Bio-Rad, Richmond, Calif.). Routinely, the efficiency of detergent removal is 90% for the ion retardation column and 98% for Extracti-gel. Where a 10% starting concentration of detergent is diluted to a concentration of 1%, application to the former results in a final detergent concentration of approximately 0.1% and application to the latter results in a final detergent concentration of approximately 0.02%. Thus, both approaches routinely result in a solution containing less than 1% of the detergent concentration of the starting material (and further reductions can be achieved by applying the flow through to the detergent removing means).

In another embodiment the present invention contemplates removal of bacterial endotoxin, which is a pyrogen, from solubilized inclusion body proteins. Removal of pyrogens is necessary to meet safety standards for injection of substances into humans. Some methods of endotoxin removal are based upon size separation and the fact that endotoxins form high molecular weight aggregates. However, in the presence of detergents, endotoxin aggregates may dissociate, so that sizing methods for separating endotoxins will be useless (A. C. Issekutz, J. of Immunological Methods, 61:275–281 (1983)). The method of the present invention solubilizes inclusion body proteins in greater than 2% anionic detergent, removes substantially all of the detergent, and removes endotoxin from the protein solution using an affinity column with binding affinity for the endotoxin. The affinity column comprises an antibiotic which has endotoxin-binding capacity immobilized on a support. This method is useful for removal of aggregated or dissociated forms of endotoxin.

II. Injecting Solubilized Inclusion Body Recombinant Protein into Vertebrates to Elicit Antibodies The present invention contemplates immunizing vertebrates with solubilized inclusion body protein. It is not intended that the present invention be limited to any particular proteins. Proteins from all sources are contemplated as immunogens. For example, toxin proteins and surface proteins from bacterial, viral, fungal, and parasitic sources may be used to immunize vertebrates for vaccination or diagnosis. Similarly, allergens may be used to immunize individuals for desensitization or diagnosis.

It is not intended that the present invention be limited to a particular mode of immunization; the present invention contemplates all modes of immunization, including subcutaneous, intramuscular, intraperitoneal, and intravascular injection.

The present invention further contemplates immunization with or without adjuvant. (Adjuvant is defined as a substance known to increase the immune response to other antigens when administered with other antigens.) If adjuvant is used, it is not intended that the present invention be limited to any particular type of adjuvant—or that the same adjuvant, once used, be used all the time. While the present invention contemplates all types of adjuvant, whether used separately or in combination, the preferred use of adjuvant is the use of complete Freund's adjuvant followed sometime later with incomplete Freund's adjuvant.

When immunization is used, the present invention contemplates a wide variety of immunization schedules. In one embodiment, a vertebrate is administered solubilized inclusion body protein on day zero and subsequently is administered solubilized inclusion body protein in intervals thereafter. It is not intended that the present invention be limited by the particular intervals or doses. Similarly, it is not intended that the present invention be limited to any particular schedule for collecting antibody.

The present invention also contemplates immunization of human individuals with compounds comprised of solubilized inclusion body protein. Products intended for administration to humans must be free of extraneous material except that which is unavoidable in the manufacturing process. 21 CFR §610.13. Some protein solubilization methods (e.g., urea) require that the solubilizing agent remain in solution with the protein because removal of the solubilizing agent causes inclusion body protein to precipitate. Unlike those methods, the present invention provides for the removal of the solubilizing detergent and, surprisingly, the maintenance of protein solubility. In this manner, protein solution for injection into humans is free of solvent impurities and can be prepared at a concentrated protein dosage.

III. Purifying Polyclonal Antibodies by Binding to a Matrix of Antigenic Inclusion Body Protein The present invention contemplates purifying antibody preparations, including monoclonal and polyclonal antibodies, utilizing immunoaffinity purification. Immunoaffinity purification is separation based on the affinity of antibody for specific antigen(s); antibody that binds to specific antigen(s) is separated from antibody that does not bind (under the conditions used). The present invention contemplates the use of immunoaffinity purification to isolate purified antibodies or to cross-absorb polyclonal antibody preparations to remove unwanted antibody populations.

The present invention contemplates immunoaffinity purification of antibody preparation raised against solubilized inclusion body protein. The immunoaffinity purification utilizes an "antigen matrix" prepared by attachment of resin to solubilized inclusion body protein, preferably by covalent attachment. In one embodiment, the material for the insoluble support (hereinafter resin) takes the form of spherical beads. In a preferred embodiment, the resin is a synthetic polymer capable of forming a gel in aqueous media (e.g., agarose). In a preferred embodiment the resin is aldehyde activated agarose. The inclusion body protein is chosen so as to bind the antibody of interest.

Antibody to be purified is applied in solution to the antigen matrix. The solution passes through the antigen matrix and comprises the "flow through." Antibody that does not bind, if present, passes with the solution through the antigen matrix into the flow through. To eliminate all non-binding antibody the matrix is "washed" with one or more wash solutions which, after passing through the matrix, comprise one or more "effluents." "Eluent" is a chemical solution capable of dissociating antibody bound to the antigen matrix (if any). The dissociated antibody is eluted from the antigen matrix in the eluent which, after passing through the matrix, comprises the "eluate." The eluate contains purified antibody.

The immunoaffinity purification of the present invention provides a number of benefits. First, the immunoaffinity purification of the present invention provides for maximum attachment of the antigen to the resin, i.e., high attachment efficiency. Second, the immunoaffinity purification of the present invention provides for recovery of as much as possible of a reactive antibody from total unpurified antibody, i.e., the quantity of purified reactive antibody is optimized. The term "reactive antibody" refers to antibodies which bind the solubilized inclusion body antigens, whether in native form or attached to the matrix.

Experimental

The following examples serve to illustrate certain preferred embodiments and aspects of the present invention and are not to be construed as limiting the scope thereof.

In the disclosure which follows, the following abbreviations apply: °C. (degrees Centigrade); g (gravitational field); vol (volume); w/v (weight to volume); v/v (volume to volume); DNA (deoxyribonucleic acid); cDNA (complimentary DNA); p (plasmid); µl (microliters); ml (milliliters); µg (micrograms); mg (milligrams); M (molar); mM (milliMolar); nm (nanometers); kdal (kilodaltons); $M_r$ (relative mobility); $OD_{280}$ (optical density at 280 nm); BSA (bovine serum albumin; EDTA (ethylene diamine tetra-acetic acid); FITC (fluorescein isothiocyanate); CFA (complete Freund's adjuvant); IFA (incomplete Freund's adjuvant); HCl (hydrochloric acid); IPTG (isopropyl β-D- thiogalactopyranoside); IgG (immunoglobulin G); LB (Luria Broth); PEG (polyethylene glycol); $Na_2CO_3$ (sodium carbonate); NaCl (sodium chloride); $NaCNBH_3$ (sodium cyanoborohydride); SDS (sodium dodecyl sulfate); $Na_2PO_4$ (sodium phosphate); Tris (tris (hydroxymethyl)aminomethane); PMSF (phenylmethylsulfonylfluoride); BBS-Tween (borate buffer containing 1M NaCl and 0.1% Tween (v/v); PBS (phosphate buffered saline); PPBS (phosphate buffered saline containing 1 mM PMSF); PPBS (phosphate buffered saline containing 10 mg/ml bovine serum albumin (Sigma) and 0.1% Triton X-100); PAGE (polyacrylamide gel electrophoresis); Tween (polyoxyethylenesorbitan); NBT (nitro blue tetrazolium); BCIP (5-bromo-4-chloro-3-indolyl phosphate); ac (achaete); ftz (fushi tarazu); gt (giant); h (hairy); hb (hunchback); kni (knirps); Kr (Krüppel); sc (scuta); tll (tailless); *E. coli* (*Escherichia coli*); BioRad (BioRad, Richmond, Calif.); Fisher Biotech (Fisher Biotech, Springfield, N.J.); GIBCO (GIBCO, Grand Island, N.Y.); Life Technologies (Life Technologies, Bethesda, Md.); Isco (Isco; Lincoln, Nebr.); Pierce (Pierce, Rockford, Ill.), Sigma (Sigma Chemical Co., St. Louis, Mo.); Sterogene Biochemicals (Sterogene Biochemicals, San Rafael, Calif.); Vector Labs (Vector Labs, Burlingame, Calif.); Zeiss (Carl Zeiss, Oberkochen, Germany).

Quantification of protein solubilization and coupling efficiency was performed by densitometric scanning of SDS-PAGE gels using samples taken before manipulations as the 100% control value. Comassie blue stained gels were scanned on an Isco scanning gel densitometer at a wavelength of 580 nm. The areas under each protein peak were calculated to determine relative peak size.

EXAMPLE 1

Induction of Recombinant Heterologous Proteins and Isolation of Inclusion Bodies To determine the best means for producing large quantities of heterologous proteins in bacteria, various host strains and methods of inclusion body isolation were examined. The objective was to obtain the greatest quantity of heterologous protein in insoluble form while removing host bacterial polypeptides. Example 1 involved a) expression of heterologous proteins in different host strains, b) isolation of inclusion body preparations largely consisting of the heterologous protein of interest, and c) release of bacterial proteins from inclusion bodies.

a) Expression of heterologous proteins in different host strains. Plasmid DNA of the pET-3 vector (Rosenberg et al., Gene 56:125 (1987)), into which a full-length cDNA encoding the entire fushi tarazu (ftz) protein of Drosophila had been inserted (A. S. Laughon, and M. P. Scott, Nature 310:25 (1984)), was introduced into the three bacterial strains BL21 (DE3), BL21 (DE3) pLysS, and BL21 (DE3) pLysE (F. W. Studier et al., Methods in Enzymology 185:60–89 (1990)) according to standard procedures.

Figure 2:
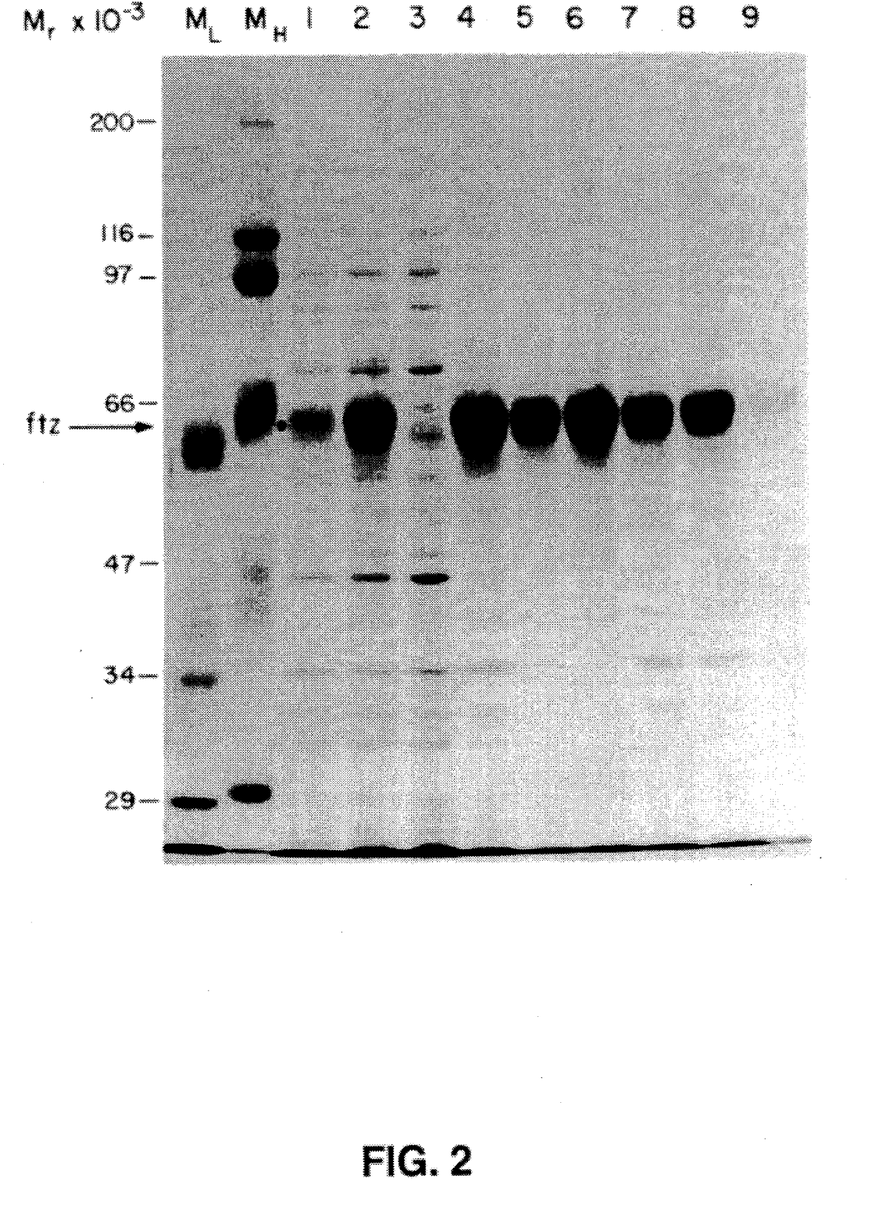
FIG. 2 shows SDS-PAGE analysis of inclusion body protein pellet washed with various solvents.

Individual colonies of each strain were selected upon the appropriate antibiotic-containing agar media and grown overnight at 37° C. in 5 ml of liquid LB containing the appropriate antibiotic(s). After the culture became stationary, the culture was diluted by adding 50 µl of culture to 4.95 ml of fresh LB containing the appropriate antibiotics and grown for another 2 hr at 37° C., after which the cells were harvested by centrifugation. The spent media was then discarded, and the cells resuspended in 1/12th of the original culture volume in 80 mM Tris-HCl pH 6.9, 2% SDS, 0.1M dithiothreitol, 0.004% (w/v) bromophenol blue (SDS sample buffer), vortexed vigorously, heated to 100° C. for 5 minutes and the lysate clarified by centrifugation, 20–25 µl of lysate from each strain were analyzed by SDS PAGE (FIG. 2). The highest level production of the ftz protein occurred in the BL21 (DE3) pLysS strain (lane 2) followed by the BL21 (DE3) (lane 1) and BL21 (DE3) pLysE (lane 3) strains. Experiments with other heterologous proteins indicated that the strains which produced the highest levels of each protein were not predictable and needed to be determined empirically.

b) Isolation of inclusion bodies. The ftz-expressing BL21 (DE3) LysS strain was utilized to investigate means of isolating inclusion bodies consisting largely of heterologous (in this case, ftz) protein. One ml of a saturated overnight culture of this strain was diluted into 100 ml of LB containing the appropriate antibiotics, grown for 2 hr, IPTG added to 0.5 mM, the culture grown for an additional 2 hr, and the bacteria harvested by centrifugation at 13,000× g for 10 minutes. The cells were resuspended in 5 ml of 50 mM Tris-HCl, 150 mM NaCl, 1 mM EDTA, pH 7.2 and chilled on ice. Lysozyme (Sigma) was added to a final concentration of 0.25 mg/ml and the incubation was continued for 20 minutes. The mixture was sonicated thoroughly with four 15 second bursts and five 1 ml aliquots were centrifuged for 4 minutes in an Eppendorf microcentrifuge in order to obtain inclusion body pellets.

c) Release of bacterial proteins from inclusion bodies. Various reagents were tested for their ability to release host proteins from the inclusion bodies while leaving the heterologous protein insoluble. In the 50 mM Tris, 150 mM NaCl, 1 mM EDTA, pH 7.2 buffer, five different solvents, solvent concentrations, or solvent mixtures were tested including i) 0.1% SDS/1% Triton X-100/1% sodium deoxycholate; ii) 0.5M guanidine-HCl; iii) 1.0M guanidine-HCl; iv) 2.0M guanidine-HCl; and v) 0.1% SDS. Five identical inclusion body pellets were suspended in 0.5 ml of each of these solutions, repelleted, suspended in a second 0.5 ml of the same solution, repelleted and dissolved and heated 5 minutes at 100° C. in SDS sample buffer. A 20 µl aliquot of each sample was analyzed by SDS-PAGE. FIG. 2 shows that maximum recovery of ftz protein with minimum host polypeptides was obtained by suspending the inclusion bodies in 0.1% SDS/1% Triton X-100/1% sodium deoxycholate (lane 6). In contrast, 0.1% SDS caused a decrease in recovery of ftz protein in the pellet (lane 5) and 2.0M guanidine solubilized the cell proteins completely (lane 9). Lower concentrations of guanidine, 0.5M (lane 7) and 1.0M (lane 8), were less effective than the SDS/Triton X-100/ sodium deoxycholate mixture in removing host polypeptides from the inclusion body pellets. Therefore, in all subsequent examples, the SDS/Triton X-100/sodium deoxycholate treatment was used to wash host polypeptides from all inclusion body preparations.

EXAMPLE 2

Solubilization and Recovery of Heterologous Proteins from Bacterial Inclusion Bodies In order to obtain soluble protein from bacterial inclusion bodies to be used for the preparation of immunogens or antigen matrices, several solvents were tested for their ability to dissolve heterologous proteins such that the heterologous protein would remain soluble after removal of the solvent by dialysis.

Inclusion bodies containing ftz protein were prepared as described in Example 1 and washed twice with 50 mM Tris-HCl, pH 7.2, 150 mM NaCl, 0.1% SDS/1% Triton X-100/1% sodium deoxycholate to remove associated host proteins. The inclusion bodies were then dissolved in either 1) buffer containing 8M urea; ii) buffer containing 4M guanidine-HCl; or iii) 10% SDS. While urea and guanidine were found to be effective solvents at the concentrations tested, upon their removal by dialysis the vast majority of dissolved protein reprecipitated and was, therefore, not useful for further manipulations requiring aqueous soluble protein (data not shown). On the other hand, SDS proved to be both an effective solvent, and, surprisingly, no precipitate formed upon its removal by dialysis against PPBS (10 mM $NaPO_4$ pH 7.2, 150 mM NaCl containing 1 mM PMSF). Therefore, the preferred method of solubilizing inclusion bodies consisted of treatment with 10% SDS, with heating if necessary, dilution into PPBS to bring the SDS concentration to 1%, followed by exhaustive dialysis at room temperature against PPBS containing 0.05% SDS, PPBS containing 0.01% SDS, and finally PPBS alone. The protein solution was then stored at 4° C. until further use. Some residual SDS sometimes precipitated upon storage at 4° C. but was readily redissolved upon warming to room temperature. Protein solutions stored in this manner were observed to be stable for a minimum of several months. Furthermore, this solution was free of reactive amine groups such as those present in urea and guanidine that would interfere with antigen matrix attachment chemistries that require free amino groups (see Example 5).

Figure 3:
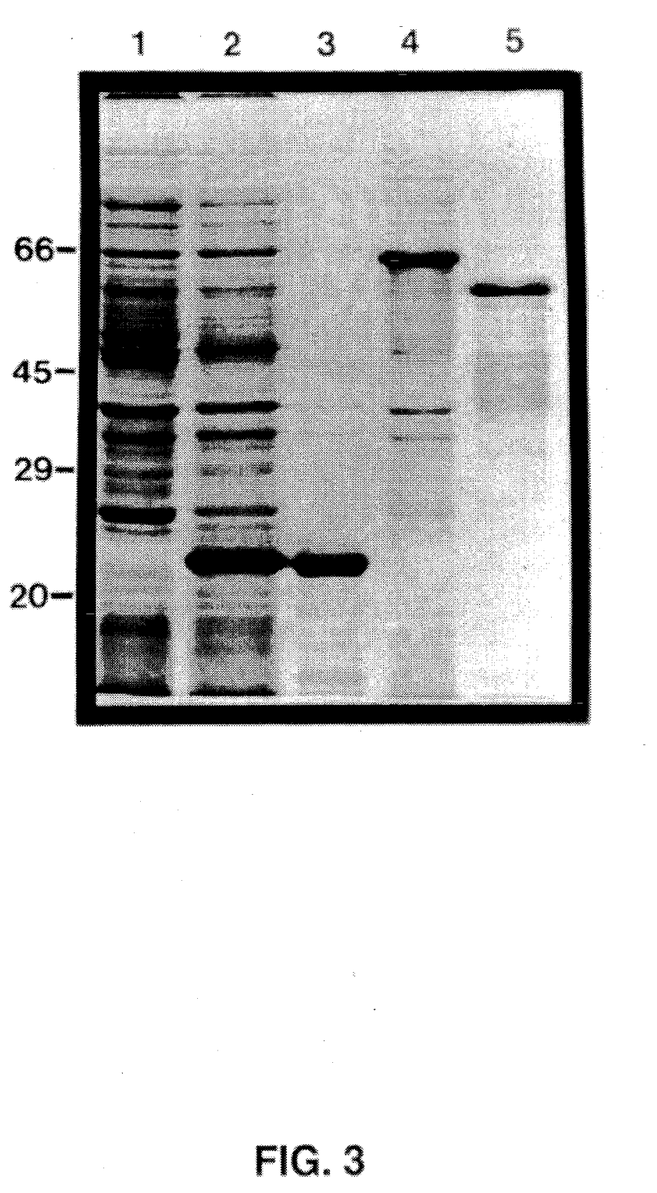
FIG. 3 shows SDS-PAGE analysis of three Drosophila recombinant proteins purified from inclusion bodies.

Numerous other proteins in addition to the ftz polypeptide were purified from inclusion bodies utilizing the preferred method above including fragments of or the entire Drosophilia Krüppel (Kr), achaete (ac), hairy (h), scuta (sc), hunchback (hb), giant (gt), tailless (tll), and knirps (kni) proteins. The purification achieved from the initial *E. coli* cells by this method is illustrated in FIG. 3 for three of these proteins which differ in size and structure ($M_r$ range is 15–60 kdal). Lanes 1 and 2 show total proteins from *E coli* carrying the recombinant ac gene: uninduced (lane 1), and induced with IPTG (lane 2). Lanes 3–5 show purified inclusion body protein for ac (lane 3), ftz (lane 4), and Kr (lane 5).

EXAMPLE 3

The Effect of SDS Concentration, Protein Concentration, and Temperature on Solubilization of Inclusion Body Protein The influence of (a) SDS concentration, (b) protein concentration, and (c) heat, on the solubilization of recombinant inclusion body proteins was investigated by dissolving inclusion bodies in SDS solution, separating the protein by SDS-PAGE, and staining the gels for quantitative analysis of protein solubilization.

Figure 4A:
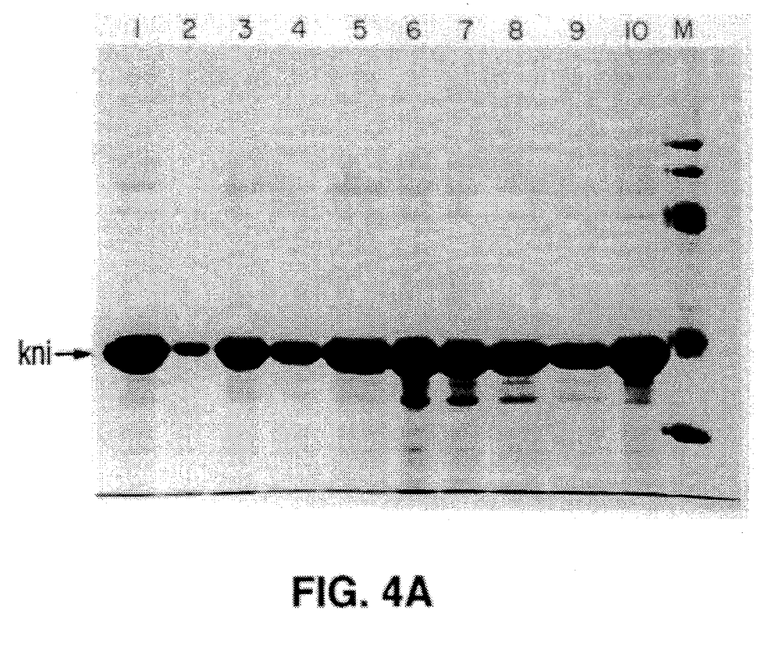
FIG. 4A shows analysis of two protein concentrations of kni protein.

(a) SDS Concentration. Inclusion bodies containing kni protein were prepared as described in Example 1b and washed with SDS/Triton X-100/sodium deoxycholate solution. 100 μl aliquots of the inclusion bodies, suspended in the wash solution, were pelleted by centrifugation and the wash solution was discarded. The inclusion bodies were resuspended in 50 μl of 10 mM $NaPO_4$ pH 7.2, 150 mM NaCl containing 0.5%, 2%, 5%, and 10% SDS (w/v) and heated for 30 min at 100° C. The mixtures were spun in a microcentrifuge and a sample, equivalent to 0.5 μl of each supernatant, was analyzed by SDS-PAGE with optical density scanning of the stained protein bands (FIG. 4A). Of the total amount of kni protein present in the inclusion bodies (lane 1), less than 25% was solubilized in the 0.5% SDS sample (lane 2). Approximately 80% of the protein was solubilized in the 2% SDS sample (lane 3) and greater than 95% of the protein was solubilized in the 10% SDS sample (lane 5).

The results show that even with heating for 30 minutes, there is incomplete solubilization of kni protein in the 0.5%, 2% and 5% SDS samples. The most complete solubilization was obtained with 10% SDS. The 5% sample in this experiment solubilized less than the 2% SDS sample. The reduced solubility of this sample may reflect the trade off between viscosity and solubility. Inclusion bodies contain adventitiously-bound protein, membranes, and nucleic acids. As these components dissolve in higher concentrations of SDS, the viscosity of the solution increases, and the solubility of the proteins appears to lessen until the SDS concentration reaches such a level that all components are dissolved effectively.

(b) Protein concentration. The effect of protein concentration on solubilization was explored by repeating the solubilization study at a higher protein concentration. The samples illustrated in FIG. 4A, lanes 2–5, contained about 10 μl packed volume of inclusion bodies suspended in 50 μl SDS solution. When the same packed volume of inclusion bodies is dissolved in 500 μl of SDS solution and heated as before, the inclusion bodies are more than 75% solubilized in 0.5% SDS (lane 7), 2% SDS (lane 8), 5% SDS (lane 9), and 10% SDS (lane 10), although, once again the 10% SDS sample exhibited the greatest degree of solubilization (>95% solubilization). Therefore, inclusion body protein concentration affects the degree of solubilization attained at different SDS concentrations. At higher inclusion body concentrations, the viscosity effects are more pronounced than at lower concentrations.

Figure 4B:
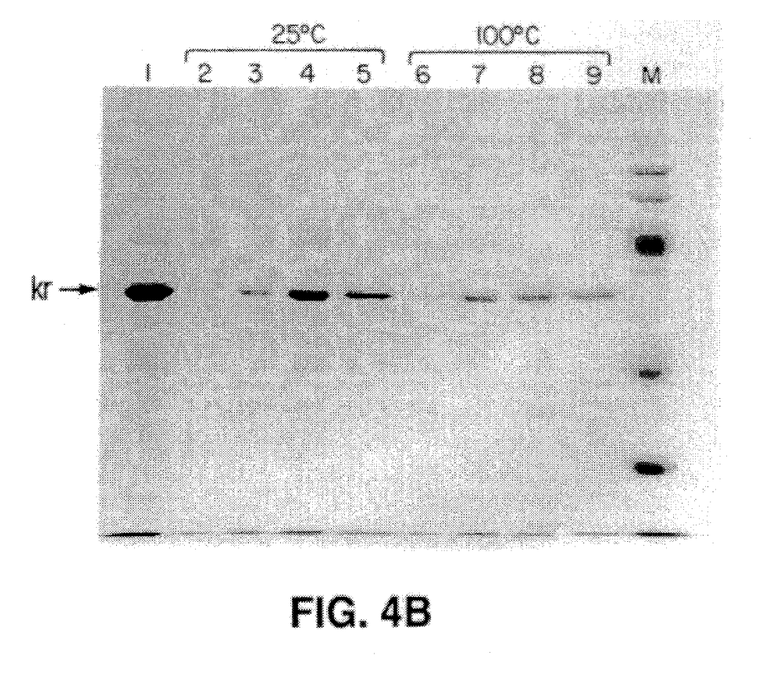
FIG. 4B shows analysis of kr protein solubilized at two different temperatures.

(c) Heating. The amount of inclusion body produced by host cells is highly variable when different recombinant proteins are expressed. Likewise, the viscosity of solubilized protein solutions for different proteins is also variable. In order to validate the observations from Example 3a and 3b for another protein, inclusion bodies containing the Kr protein were prepared as described in Example 1b. Equal aliquots of washed inclusion bodies were suspended in 100 μl of 10 mM $NaPO_4$ pH 7.2, 150 mM NaCl containing 0.5%, 2%, 5%, or 10% SDS and incubated at room temperature or 100° C. for 30 min. Samples, equivalent to 0.125 μl of each supernatant, were analyzed by SDS-PAGE (FIG. 4B). At room temperature, the amount of protein solubilized increased as the SDS concentration increased from 0.5% (less than 5% dissolved, lane 2) to 2% (approximately 30% dissolved, lane 3) to 5% (greater than 90% dissolved, lane 4) to 10% (greater than 90% dissolved, lane 5). At 100° C., 0.5% SDS was ineffective (less than 10% dissolved, lane 6) but 2% SDS (lane 7), 5% SDS (lane 8), and 10% SDS (lane 9) were all effective (greater than 90% dissolved).

These results demonstrate the dependence of inclusion body protein solubility on SDS concentration, temperature, and initial protein concentration. The results indicate that the most generally effective method of protein solubilization is suspension of inclusion body protein in 10% SDS, with heating at 100° C. for 30 min. This method is effective at high protein concentrations (e.g., greater than 10 mg/ml) as well as low concentrations (e.g., less than 1 mg/ml).

EXAMPLE 4

Influence of SDS Detergent Concentration on Protein Coupling Efficiency to an Affinity Matrix One rationale for removing SDS from the inclusion body preparations in Example 2 was concern whether high concentrations of SDS would affect the efficiency of protein coupling to affinity matrices. In order to determine whether excess SDS would influence coupling efficiencies, the attachment of a well-characterized protein was studied over a range of detergent concentrations.

Bovine serum albumin (BSA) was dissolved at a concentration of 1 mg/ml in PBS containing 0%, 0.5%, 2%, 5%, or 10% (w/v) SDS. Five ml of each protein solution was incubated with 5 ml of Actigel A (Sterogene Biochemicals) in the presence of 10 mM NaCNBH$_3$ at room temperature overnight. The uncoupled fraction of each mixture was collected by filtration and analyzed for uncoupled BSA by OD$_{280}$. The coupling efficiencies of each mixture was calculated by determining the percent of protein attached to the affinity gel and are shown in Table 1.

TABLE 1

Effect of SDS concentration on coupling efficiency of a protein solution

| % SDS Concentration | Coupling Efficiency |
|---|---|
| 0 | 71 |
| 0.5 | 23 |
| 2.0 | 42 |
| 5.0 | 32 |
| 10.0 | 23 |

As can be seen from Table 1, SDS concentrations from 0.5%–10% all diminished the coupling efficiency of BSA significantly. Therefore, it is clearly desirable to remove substantially all of the SDS (i.e., greater than 99.5%) from protein solutions before attachment to affinity matrices.

EXAMPLE 5

Covalent Attachment of Heterologous Proteins Solubilized from Bacterial Inclusion Bodies to an Affinity Matrix The SDS solubilized, dialyzed proteins, as described in Example 2, each contain potentially reactive amine groups. To determine whether these groups are available in the PPBS buffer environment, the coupling of several proteins to an amine-reactive antigen affinity matrix was investigated.

Five ml of three different solutions containing 1–3 mg of ftz, Kr, and ac protein, respectively, prepared as described in Example 2, were each incubated with 5 ml of Actigel A, an agarose-based aldehyde-activated affinity matrix, in the presence of fresh 10 mM NaCNBH$_3$ (Sigma) at room temperature overnight. The uncoupled fraction of each mixture was collected by filtration and analyzed by quantitative SDS polyacrylamide gel electrophoresis. Samples of the pre- and post-coupling reactions of each protein were loaded onto a 10% gel, electrophoresed, and the gel stained with Comassie Blue. After destaining, each gel was scanned densitometrically and the area under each peak calculated. The results showed that 85% of the initial ftz protein, 60% of the initial Kr protein, and 78% of the initial ac protein were covalently coupled to the Actigel A matrix. These results indicate that proteins prepared in the manner described in Example 2 in buffers free of amino groups can be effectively coupled to antigen affinity matrices.

EXAMPLE 6

Immunization of Vertebrate Animals with Heterologous Proteins Solubilized from Bacterial Inclusion Bodies To investigate whether heterologous proteins purified and solubilized from bacterial inclusion bodies as described in Example 2 could elicit specific antibody production in vertebrate animals, rabbits, mice and chickens were immunized with the following SDS-solubilized, dialyzed heterologous proteins.

rabbits: ftz, Kr, kni, gt, tll, and hb mice: ac and h chickens: ac

Example 6 involved a) immunization of vertebrates with solubilized protein and b) collection of immune serum (rabbits and mice) or yolk immunoglobulin (chickens) for further analysis.

a) Immunization of vertebrates. The schedules for immunization with antigen were as follows: i) Pairs of rabbits were immunized separately on day 0 with 1–5 mg of solubilized ftz, kr, kni, gt, tll, or hb protein prepared from bacterial inclusion bodies as described in Example 2. The final protein-containing dialysate was emulsified in a 4:5 (vol/vol) ratio with CFA (Gibco) to create a long-lasting antigen depot. Rabbits were injected at 4–6 sites subcutaneously along the back. The rabbits were boosted on days 14, 21 and approximately every fourteen days thereafter until the conclusion of the experiment with 1–5 mg of solubilized protein emulsified in a 4:5 ratio with IFA (Gibco) at 4–6 sites subcutaneously along the back. ii) Mice were immunized on day 0 with 25–50 µg of solubilized ac or h protein emulsified in a 4:5 (vol/vol) ratio of dialysate to CFA at two sites intraperitoneally. On days 14, 21 and monthly thereafter until the conclusion of the experiment, the mice were boosted by intraperitoneal injection with 25–50 mg of ac or h emulsified in a 4:5 ratio of IFA. iii) Laying hens were immunized on day 0 with 1 mg of solubilized ac protein emulsified in a 4:5 (vol/vol) ratio of CFA. Injections were subcutaneous and made along the breast and wing. On days 14, 21 and approximately every fourteen days thereafter, the chickens were immunized with 1 mg of ac protein emulsified in a 4:5 ratio of IFA at multiple subcutaneous sites along the breast and wing.

b) Antibody collection. i) Rabbit whole blood was collected on days 28, 42, and every fourteen days thereafter from the ear vein. Serum was obtained by clarifying the retracted, clotted blood that was allowed to stand overnight at 4° C. Sodium azide was added to the serum to a concentration of 0.02% (w/v) and the serum was stored at either 4° C. or −20° C. ii) Mice were bled from the tail vein and serum obtained as described above for rabbit blood. iii) Eggs from laying hens were collected and stored at 4° C. Whole yolk immunoglobulin was obtained by polyethylene glycol precipitation exactly as described by B. S. Thalley and S. B. Carroll, BioTechnology 8:934–938 (1990). See also: U.S. patent application Ser. No. 7-429791, hereby incorporated by reference.

EXAMPLE 7

Affinity Purification of Polyclonal Antibodies Raised Against Solubilized Recombinant Inclusion Bodies on Antigen Matrices of Covalently Attached, Solubilized Protein Antisera were obtained from animals immunized with heterologous proteins solubilized from bacterial inclusion bodies (see Example 6). The antisera were purified on antigen matrices of covalently-attached protein (see Example 5). Quantitation of the antigen-specific antibody titer showed that all animals produced specific antibody. Purification and quantitation of antisera from (a) rabbit immunized with ftz protein, (b) chicken immunized with ac protein, and (c) rabbits and chickens immunized with various proteins are described below.

a) Rabbit anti-ftz antibody. Sera, 40 ml total, drawn from two rabbits 79 days after the initiation of the immunization schedule, was applied to a 5 ml column of Actigel-A to which approximately 5 mg of solubilized ftz protein had been attached. The column was loaded at a rate of 1 ml/min. The initial unbound fraction was washed free with PBS, BBS-Tween, and PBS successively until no protein was detected by monitoring the $OD_{280}$ of the effluent. Bound antibody was eluted by applying 4M guanidine-HCL, 10 mM Tris pH 8.0 to the column. 16 ml of eluate were dialyzed extensively against several changes of PBS and the total antibody concentration estimated by $OD_{280}$ where an $OD_{280}$ of 1.4=1 mg/ml IgG. The eluate contained 6.55 mg of specific antibody representing a serum titer of 164 µg/ml.

b) Chicken anti-ac antibody. PEG-purified yolk immunoglobulin (35 ml), prepared from eggs collected 40 days after the first immunization was applied to a 5 ml column containing approximately 5 mg of achaete protein covalently attached to Actigel A affinity matrix. The column was washed free of protein and eluted as in (a). The chicken anti-ac IgG was dialyzed against PBS and quantitated spectrophotometrically, yielding a titer of 37 µg of ac-specific antibody per ml of egg yolk.

c) Other antisera. Antisera against the Kr, hb, gt, tll, and kni proteins, and other preparations of chicken anti-ac antibody were affinity purified on their respective antigen matrices as described above and the specific antibody titers estimated spectrophotometrically. The titers from the different sera are shown in Table 2. All animals responded to immunizations with all of the proteins and, with additional immunizations, titers increased (i.e., all of the inclusion body proteins were immunogenic in animals and antigenic on affinity matrices).

TABLE 2

Specific antibody titers of sera from animals immunized with heterologous proteins solubilized from bacterial inclusion bodies

| Immunizing Protein | Animal Species | Days Assayed | Titer (µg/ml) |
|---|---|---|---|
| ftz | rabbit | 79 | 164 |
| Kr | rabbit | 220 | 118 |
| hb | rabbit | 41 | 313 |
| kni | rabbit | 44 | 200 |
| tll | rabbit | 58 | 413 |
| gt | rabbit | 56 | 640 |
| ac | chicken | 40 | 37 |
| ac | chicken | 119 | 155 |
| ac | chicken | 138 | 254 |

EXAMPLE 8

Figure 5A:
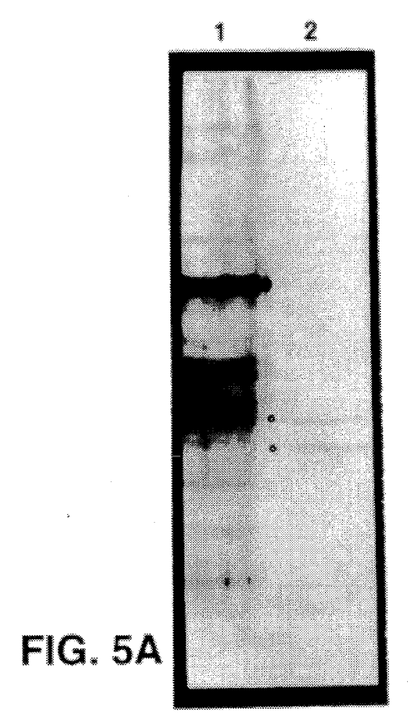
FIG. 5A shows the reactivity of anti-Kr antibody with Kr and ftz recombinant proteins purified from inclusion bodies.
Figure 5B:
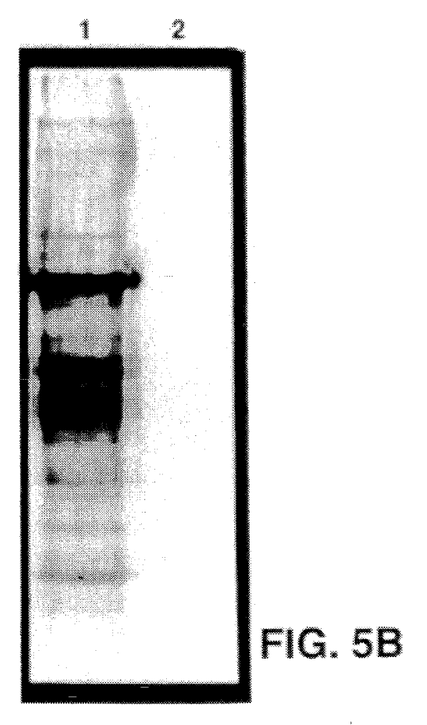
FIG. 5B shows the reactivity of anti-Kr antibody, after passage through an ftz inclusion body protein column, with Kr and ftz recombinant proteins purified from inclusion bodies.
Figure 6A:
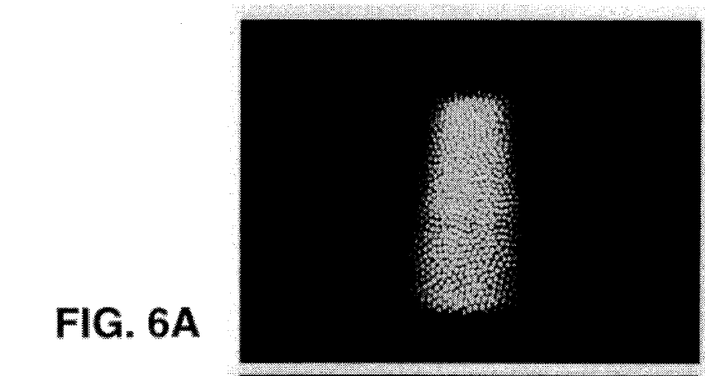
FIGS. 6a, b, c, and d are photographs of embryos stained with antibody preparations raised against the inclusion body protein: (a) Kr, (b) gt, (c) hb, and (d) kni, showing specific fluorescence within nuclei due to binding of the antibody with native (a) Kr, (b) gt, (c) hb and (d) kni proteins.
Figure 6B:
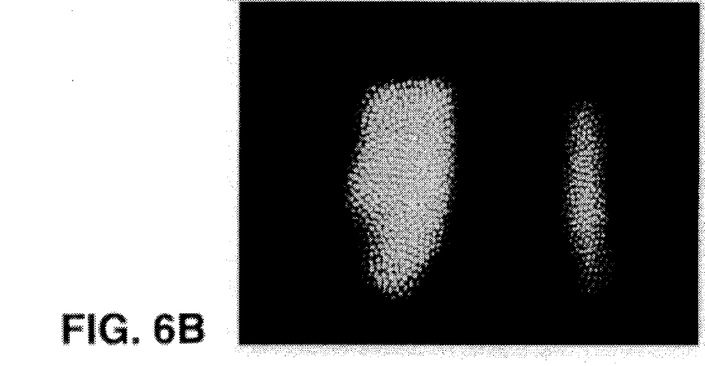
Figure 6C:
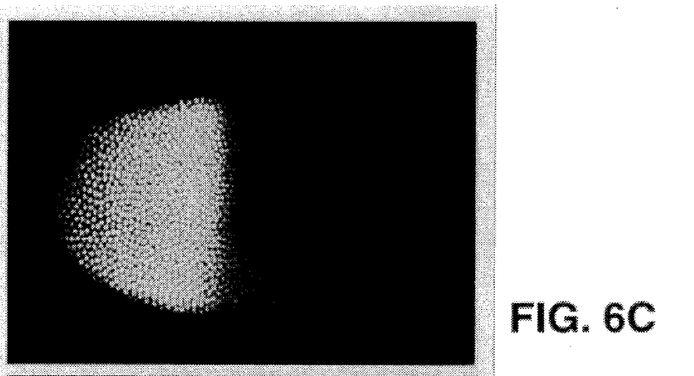
Figure 6D:
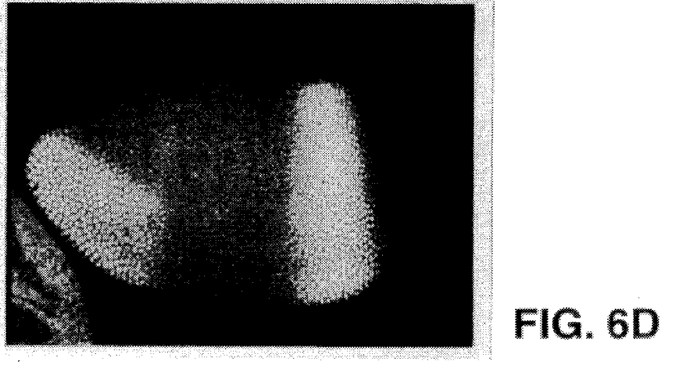

Purification of Antibodies Against a Single Recombinant Protein by Cross-absorption on Matrix of Heterologous Recombinant Protein The protein used to raise and purify antibodies as described in Examples 6 and 7 were not always highly pure and contained host (*E. coli*) proteins in addition to the recombinant protein (See FIG. 3). Example 8 involves: a) investigation of whether antibody to host proteins were indeed present, and b) development of a means to remove these antibodies, yielding a preparation largely specific for the recombinant protein of interest.

a) Detection of antibodies to host proteins on Western blots. Two different inclusion body preparations containing 1–3 mg/ml of Kr (FIG. 5, lane 1) and ftz (FIG. 5, lane 2) proteins were electrophoresed on a 10% SDS polyacrylamide gel and transferred to nitrocellulose paper. (H. Towbin et al., Proc. Natl. Acad. Sci. USA 76:4350–4354 (1979)). After the paper was blocked of protein-binding activity with 3% BSA in PBS, the blot was incubated with a solution containing 1 µg/ml rabbit anti-Kr antibody (prepared as described in Example 7). After two hours, the blot was washed with PBS, BBS-Tween, and PBS and incubated with a 1:1000 dilution of goat anti-rabbit IgG-alkaline phosphatase conjugate (Fisher Biotech) for two hours. The blot was washed again as above and the color signal developed with NBT/BCIP in 50 mM $Na_2CO_3$, pH 9.5. As shown in FIG. 5A, Lane 1, the anti-Kr antibody detects numerous proteins present in the Kr inclusion body preparation (these are the Kr protein, its degradation products, and possibly multimers of the Kr protein) as well as two polypeptides present in the ftz inclusion body preparation (FIG. 5A, Lane 2). This suggests that the two polypeptides are host proteins since they are present in both the ftz and kr preparations and suggests that the antibodies binding these host proteins were elicited in animals and recovered by the method of Example 7.

b) Removal of antibodies to host proteins by cross-absorption with heterologous inclusion body proteins. Rabbit anti-Kr antibody in PBS (3.4 mg), purified as in Example 7, was applied to a 5 ml ftz protein column, prepared as in Example 5. The column was washed with PBS and the effluent collected. Western blots were prepared as described in Example 8a, except that the antibody applied to the blot was the cross-absorbed anti-Kr antibody from the effluent. As shown in FIG. 5B, cross-absorption of the antibody, purified using inclusion body protein over a heterologous inclusion body protein column, removes host polypeptide-specific antibody (lane 2) but retains the original recombinant protein specific antibody (lane 1).

EXAMPLE 9

Verification of Antibody Reactivity with Native Proteins

To determine whether the antibodies raised and purified against detergent-solubilized inclusion body proteins do indeed recognize the corresponding native proteins, the reactivity of antibodies purified against recombinant Drosophila proteins was verified by immunohistochemistry on Drosophila embryos.

Zero to six hour old Drosophila embryos were collected, washed, dechlorinated, fixed, and devitellinized as described in S. Carroll and M. P. Scott, Cell 43:47–57 (1985). Devitellinized embryos were incubated in PBT (consisting of PBS with 10 mg/ml bovine serum albumin (Sigma) and 0.1% Triton X-100 (Sigma)) for at least three hours at 4° C. 200 µl of solutions containing 0.5 µg/ml of affinity-purified rabbit antibodies to the Kr, gt, hb, and kni proteins in PBT, prepared as described in Examples 5–8, were incubated overnight with 20 µl of embryos (settled volume) at 4° C. The embryos were washed at least six times over 2 hr with 1.5 ml of PBT, incubated with a 1:200 dilution of biotinylated goat anti-rabbit-IgG (Vector Labs) for 2 hrs at 4° C. in 200 µl of PBT, and washed again as before. 200 µl of a 1:200 dilution of FITC-conjugated streptavidin (Life Technologies) was added in PBT and incubated for 90 min. The embryos were washed with PBT six times over 90 min and twice with 50 mM Tris pH 8.8. The embryos were incubated overnight with 50 mM Tris pH 8.8 containing 10% glycerol and 0.5 mg/ml p-phenylenediamine. The embryos were then mounted on glass slides under coverslips and visualized and photographed on a BioRad MRC-600 Laser Scanning Confocal Fluorescence Microscopy System equipped with a Zeiss IM35 microscope. Specific fluorescence within nuclei of embryos stained with each antibody preparation is reflected by regional-specific patterns identical with the known patterns of hb (D. Tautz, Nature 332:281–284 (1988)), kni (J. Pankratz et al., Cell 61:309–317 (1990)), Kr (U. Gaul and H. Jäckle, Cell 50:639–647 (1987)), and gt (R. Kraut and M. Levine, Development 111:601–609 (1991)) protein expression (See FIG. 6a, 6b, 6c, and 6d, respectively). Thus, antibodies raised and purified against bacterially derived, SDS solubilized, inclusion body proteins react in situ with native counterparts of the heterologous inclusion body proteins. That the antibody binds to native protein in situ indicates that the solubilized proteins which elicited the antibodies folded into a structure antigenically similar to the native protein.

EXAMPLE 10

Endotoxin Removal

Removal of endotoxin is accomplished by means of commercially available affinity columns, such as Affi-Prep Polymyxin Support (Bio-Rad), which use an endotoxin-binding antibiotic covalently coupled to a support matrix. Sterile procedures, sterile plasticware, and pyrogen-free water are used to avoid endotoxin contamination.

5 ml of the solubilized inclusion body protein prepared as in Example 2 is applied to a 5-ml Affi-Prep Polymyxin Support column, and the column washed with 5 ml binding buffer (10 mM phosphate buffer, pH 6.0, containing 100 mM NaCl). The effluent is collected and analyzed for endotoxin by the Limulus amoebocyte lysate (LAL) assay using commercially available assay kits (e.g., Difco Laboratories, Detroit, Mich.). If necessary, the protein solution is then concentrated using an ultrafiltration apparatus (Amicon).

From the above, it is clear that the inclusion body protein solubilization method of the invention has several benefits over prior methods. The method of the invention maintains protein in solution after removal of the solubilizing agent and eliminates the need for amine-containing denaturants which interfere with protein reactivity. Additionally, the method of the invention is efficient for solubilizing proteins having widely varying solubilities and preserves the immunological activity of the protein.

I claim:

1. A method for solubilizing and maintaining the solubility of inclusion body protein, comprising:
   a) providing:
      i) inclusion body protein,
      ii) a first solution comprising between approximately 2% and 10% sodium dodecyl sulfate detergent that is substantially free of reactive amine groups,
      iii) at least a second solution that is substantially free of reactive amine groups and that contains less sodium dodecyl sulfate detergent than said first solution; and
      iv) a non-detergent-containing diluent that is substantially free of reactive amine groups;
   b) treating said inclusion body protein with said first solution at 95° C. to 100° C. so that a solubilized protein solution is produced wherein greater than 95% of said inclusion body protein is solubilized;
   c) diluting said solubilized protein solution with said non-detergent-containing diluent; and
   d) removing said detergent to a concentration of less than 0.5% by dialysis of said diluted first solution against at least said second solution under conditions such that said solubilized protein remains solubilized.

2. The method of claim 1 wherein step (a) further comprises providing successive solutions of decreasing percentage of sodium dodecyl sulfate detergent all of which contain less detergent then both said first and second solutions and which are substantially free of reactive amine groups and step (d) further comprises, after dialysis against said second solution, successively dialyzing said solubilized inclusion body protein against said successive solutions in order of decreasing detergent content.

3. The method of claim 2 wherein said first solution is approximately 10% sodium dodecyl sulfate.

4. The method of claim 1 further comprising after step (d):
   e) immunizing a vertebrate species with said solubilized protein, so that reactive antibodies are produced.

5. The method of claim 4 further comprising after step (e):
   f) purifying said reactive antibodies.

6. The method of claim 1 further comprising after step (d):
   e) attaching said solubilized inclusion body protein to an insoluble support.

7. The method of claim 6 wherein said attaching is covalent attaching.

8. The method of claim 7 wherein said insoluble support comprises a resin comprising aidehyde-activated agarose.

9. The method of claim 8 wherein greater than 50% of said solubilized protein is attached to said insoluble support.

10. A method of eliciting antibodies to solubilized inclusion body protein, comprising:
    a) providing:
       i) inclusion body protein,
       ii) a first solution comprising between approximately 2% and 10% sodium dodecyl sulfate detergent that is substantially free of reactive amine groups, and
       iii) a second solution that is substantially free of reactive amine groups and that contains less sodium dodecyl sulfate detergent than said first solution,
       iv) a vertebrate species; and
       v) a non-detergent-containing diluent that is substantially free of reactive amine groups;
    b) treating said inclusion body protein with said first solution at 95° C. to 100° C. so that a solubilized protein solution is produced wherein greater than 95% of said inclusion body protein is solubilized;
    c) diluting said solubilized protein solution with said non-detergent-containing diluent;
    d) removing said detergent to a concentration of less than 0.5% by dialysis of said diluted first solution against said second solution under conditions such that said solubilized protein remains solubilized; and
    e) immunizing said vertebrate species with said solubilized inclusion body protein, so that antibodies reactive with said inclusion body protein are produced.

11. The method of claim 10 further comprising the step:
    e) purifying said reactive antibodies.

12. The method of claim 11 wherein step e) comprises purifying said reactive antibodies by means of an antigen matrix comprising said soluble inclusion body protein covalently attached to an insoluble support.

13. The method of claim 12 wherein said insoluble support comprises a resin comprising aldehyde-activated agarose.

* * * * *